United States Patent [19]

Kling

[11] Patent Number: 5,961,509

[45] Date of Patent: Oct. 5, 1999

[54] SHAPED ABSORBENT ARTICLE AND METHOD OF MANUFACTURING THE SAME

[75] Inventor: Robert Kling, Skene, Sweden

[73] Assignee: SCA Hygiene Products AB, Goteborg, Sweden

[21] Appl. No.: 08/849,882

[22] PCT Filed: Dec. 19, 1995

[86] PCT No.: PCT/SE95/01535

§ 371 Date: Jun. 18, 1997

§ 102(e) Date: Jun. 18, 1997

[87] PCT Pub. No.: WO96/19165

PCT Pub. Date: Jun. 27, 1996

[30] Foreign Application Priority Data

Dec. 21, 1994 [SE] Sweden .................................. 9404434

[51] Int. Cl.⁶ .............................. A61F 13/15; A61F 13/20
[52] U.S. Cl. ....................... 604/385.1; 604/366; 604/370; 264/510; 264/258; 156/224
[58] Field of Search ..................................... 604/366, 385, 604/386, 387, 369, 370, 385.1; 156/192, 221, 222, 224; 264/510, 511, 512, 257, 258

[56] References Cited

U.S. PATENT DOCUMENTS

| | | | |
|---|---|---|---|
| 2,864,362 | 12/1958 | Hermanson et al. | 604/385.1 |
| 2,964,039 | 12/1960 | Johnson, Jr. et al. | 604/385.1 |
| 2,964,040 | 12/1960 | Ashton et al. | 604/366 |
| 2,964,041 | 12/1960 | Ashton et al. | 604/366 |
| 3,236,238 | 2/1966 | Morse | 604/366 |
| 3,262,451 | 7/1966 | Morse | 604/370 |
| 3,430,630 | 3/1969 | Megison et al. | 604/370 |
| 3,683,921 | 8/1972 | Brooks et al. | |
| 3,768,479 | 10/1973 | Widlund | 604/366 |
| 4,217,901 | 8/1980 | Bradstreet et al. | |
| 4,392,862 | 7/1983 | Marsan et al. | 604/366 |
| 4,681,577 | 7/1987 | Stern et al. | 604/378 |
| 4,728,381 | 3/1988 | Jezuit et al. | |
| 4,770,657 | 9/1988 | Ellis et al. | 604/385.1 |
| 4,886,513 | 12/1989 | Mason, Jr. et al. | 604/385.1 |
| 5,211,792 | 5/1993 | Carter | 156/222 |
| 5,300,055 | 4/1994 | Buell | 604/385.1 |
| 5,389,181 | 2/1995 | Vukos et al. | 152/221 |
| 5,599,334 | 2/1997 | Johnston et al. | 604/385.1 |

FOREIGN PATENT DOCUMENTS

| | | |
|---|---|---|
| 0 139 484 A1 | 5/1985 | European Pat. Off. . |
| 0 140 470A1 | 5/1985 | European Pat. Off. . |
| 0 140 471A1 | 5/1985 | European Pat. Off. . |
| 0 256 871 | 2/1988 | European Pat. Off. . |
| 0 302 523 A2 | 2/1989 | European Pat. Off. . |
| 820734 | 9/1959 | United Kingdom ............ 604/366 |
| 862185 | 3/1961 | United Kingdom ............ 604/366 |
| 2 193 100 | 2/1988 | United Kingdom . |
| 2 284 552 | 6/1995 | United Kingdom . |

Primary Examiner—Mark O. Polutta
Attorney, Agent, or Firm—Burns, Doane, Swecker & Mathis, L.L.P.

[57] ABSTRACT

A flexible absorbent article such as a nappy or a sanitary pad having an absorbent core and a three-dimensional shape. The absorbent article includes a thermoformed layer formed integrally therewith which substantially maintains said three-dimensional shape. The invention also relates to a method for manufacture of the same. The cost of production of three-dimensional absorbent products can thereby be significantly reduced and more complicated shapes can be obtained.

14 Claims, 2 Drawing Sheets

SHAPED ABSORBENT ARTICLE AND METHOD OF MANUFACTURING THE SAME

FIELD OF THE INVENTION

The present invention relates to a flexible absorbent article, having a plurality of layers, an absorbent core, and a thermoformed layer formed integrally therewith to maintain the absorbent article in a three-dimensional shape defining an open volume. The invention also relates to a method of producing such an article.

More particularly, the invention relates to absorbent articles such as absorbent garments or sanitary pads.

BACKGROUND ART

Flexible absorbent articles of the aforementioned type are known in the field of sanitary pads for example. An example of such a sanitary pad is sold under the trademark SERENITY® and is a sanitary pad which, in the relaxed state, has a U-shaped or V-shaped appearance when viewed from the side in order that the pad fits more closely to the contours of the body at the point of application. The sanitary pad has a multi-layer absorbent core with or without SAP (super absorbent polymer), which is enclosed between an impervious back sheet layer and a porous top sheet layer. The back sheet layer (comprising a foamed polymer layer) and the top sheet layer are attached to each other at their respective peripheries with the top sheet layer in a stretched state. Since the top sheet layer is in a stretched state when attached to the foamed polymer layer, it will thus ensure that the sanitary pad has a three-dimensional shape defining an open volume therewithin when in the relaxed state.

Clearly, the production operation for such a sanitary pad is quite complicated due to the need to stretch one layer and hold it in the stretched position whilst applying and attaching a further layer to it. Due to the fact that an economic production must be achieved, some shape restrictions on the product will also occur due to the manner of stretching which must not be too intricate.

Thus the invention seeks to overcome said complications by providing an article which can be manufactured substantially without stretching but which has a three-dimensional shape defining an open volume therewithin, which can be varied within wide limits. The invention also seeks to provide a corresponding method for manufacturing said product.

SUMMARY OF THE INVENTION

The aforementioned object is solved by an article having a plurality of layers, an absorbent core, and a thermoformed layer formed integrally therewith to maintain the absorbent article in a three-dimensional shape defining an open volume. Similarly, the method of producing an absorbent article including a plurality of layers including an absorbent core by adding a thermoformable net layer to one of the plurality of layers and applying heat ton one of the layers and the thermoformable net layer while the device is in a predetermined shape so as to thermoform the article into the predetermined shape is also described. The flexible absorbent article is preferably a sanitary pad or an absorbent garment, such as a nappy, the flexible absorbent article preferably has a core located between a backing sheet and a top sheet, has a core located between a backing sheet and a top sheet and a thermoformed layer between the back sheet and the top sheet, wherein the thermoformed layer is located with the absorbent member or wherein the thermoformed member is integral with the back sheet.

By using a thermoformable layer in the mariner defined, the article can be manufactured more easily and in a wider variety of shapes which are suitable for differing applications.

The invention can also be used for absorbent products designed to have a curvature in more than one direction, e.g. saddle-shaped products (which offer a better fit to the body) such as saddle-shaped sanitary pads for example.

By the term "thermoformable layer" as used in the claims and the following description is meant a layer which comprises a material, such as EVA (ethylene vinyl acetate) for example, which can be made to assume a predetermined shape in the cold state (e.g. at room temperature). The layer must then be able Lo substantially maintain this shape after being heated to a sufficient temperature (typically a temperature between 85° C. and 130° C.) for a sufficient time (e.g. between 5 to 40 seconds) and subsequently cooled (naturally or otherwise) whilst being restrained in said particular shape. Such a layer will preferably be in the form of a net of longitudinal and transverse crossing threads or fibres, but may also be in the form of a layer of particles (powder, granules or fibres) of said material arranged so as to provide a stable but flexible structure when thermoformed. Other forms of the thermoformable layer are also imaginable.

BRIEF DESCRIPTION OF THE DRAWINGS

The invention will now be described in more detail with reference to the accompanying drawings in which.

DESCRIPTION OF PREFERRED EMBODIMENTS

Figure 1:
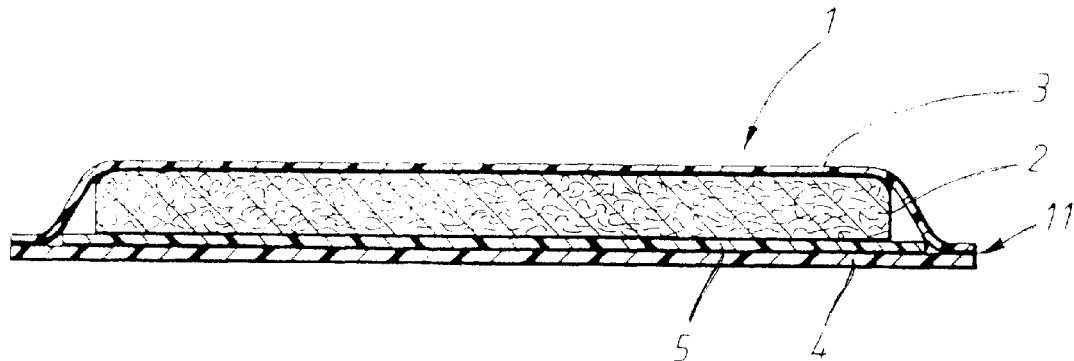
FIG. 1 shows a sectional side view of a sanitary pad during an initial stage of production of an article in accordance with the invention with the thermoformable layer positioned between the back sheet and the absorbent core.

The absorbent article according to the present invention is shown in a first embodiment in FIG. 1 having the form of a sanitary pad 1 for female use. The view in FIG. 1 however does not depict the final article, but instead merely shows an intermediate stage of production of said sanitary pad, the final product of FIG. 1 being shown in FIG. 5.

In the embodiment shown, the sanitary pad 1 comprises a top sheet 3 which is designed to be in contact with the body and which is thus porous and normally very thin. A back sheet 4 is also provided and this is normally an impervious sheet which serves to protect the wearer's clothes from staining from fluids which are passed from the body, through the porous top sheet 3 and into the absorbent core 2.

In the depicted embodiment the absorbent core 2 is a relatively thick core made from cellulosic pulp possibly containing SAP. However, thinner types of core and/or sanitary pads may also be used with this invention with or without a separate top sheet or backing sheet.

Before the top sheet layer 3 and the back sheet layer 4 are joined together at the periphery, a layer of thermoformable material 5 is placed on the inner surface of the backing sheet. The layer may be laminated to the backing sheet in a previous process, for example by the application of heat, or the layer may be added separately to the back sheet layer before application of the absorbent core 2 and held in place by the applied core 2. In order to function satisfactorily the thermoformable layer must however be integrated into the structure of the article in some way either before or after thermoforming.

The back sheet layer and the top sheet layers can be of known type. The thermoformable layer 5 is preferably in the form of a net of e.g. EVA having a small mesh size (e.g. 3×3 mm) which thus results in a net which is flexible yet sufficiently rigid to allow ease of handling.

Figure 2:
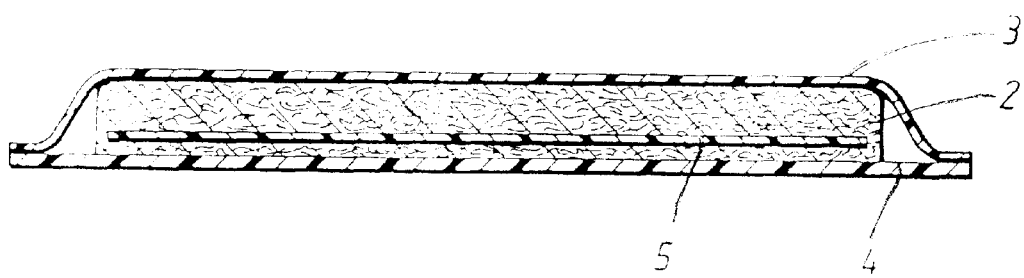
FIG. 2 shows a sectional side view similar to that of FIG. 1, but with the thermoformable layer positioned within the absorbent core.

The embodiment shown in FIG. 2 differs from that in FIG. 1 only in that the thermoformable layer 5 is positioned in the body of the absorbent core 2. Such positioning may occur by the layer being placed between two separate layers of the absorbent core which are superposed, or by the net being added during mat-building (known per se, see e.g. the mat-building/mat-forming method disclosed in e.g. EP-A-0 369 974) of the absorbent core itself.

As shown in the figure, the outer edges of the thermoformable layer are within the outer boundaries of the absorbent core 2 by a small margin at either end. This is however not a requirement and the layer 5 may extend up to or even beyond the edges of the absorbent core 2.

Figure 3:
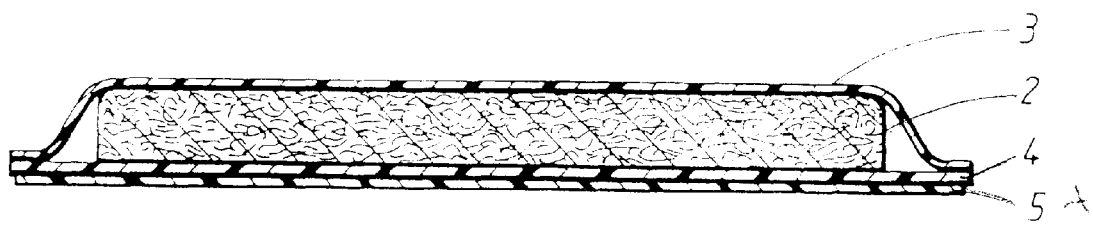
FIG. 3 shows a sectional side view similar to that of FIG. 1, but with the thermoformable layer placed on the outer side of the backing sheet.

In the embodiment shown in FIG. 3, the thermoformable layer has been attached to the underside of the back sheet 4, in which position it will be easiest to thermoform into the final product by the effect of heat. Additionally, since the outer side of the back sheet is not in contact with the body, no discomfort from the thermoformed layer will occur. Lamination of the layer 5 to the back sheet layer 4 by suitable means is preferable in this embodiment since this allows the backing sheet to be handled easily.

Whilst the thermoformable layer 5 has been shown as a single layer, the thermoformable layer may be constituted by two or more layers (not shown) which are separated from each other. For example, a single layer of thermoformable net may be attached on either side of the back sheet layer.

Additionally the back sheet layer may be a laminate structure with a plurality of layers, in which case the thermoformable layer may be positioned within the layers and held in place between the layers.

Figure 4:
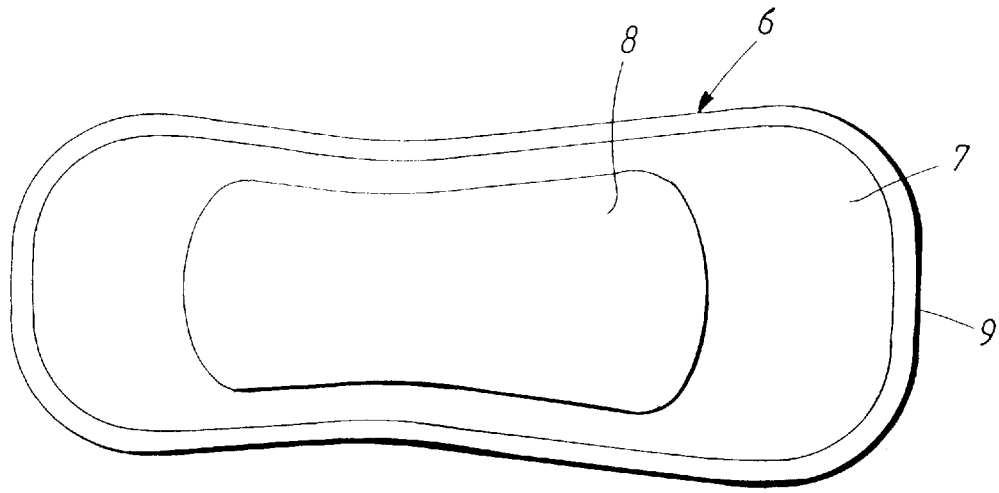
FIG. 4 shows a plan view of a typical sanitary pad shape with zones denoting where said thermoformable layer can be placed.

FIG. 4 shows a plan view of a typical sanitary pad 6 shape. within the outer boundary 9 of the sanitary pad, taco zones 7 and 8 one depicted. These zones defile examples of the extent of the area of the thermoformable layer. Thus, in order to achieve a shape as in FIG. 5 having (in a side view) only one main curved portion 10 defining the open volume, it may be sufficient to apply the thermoformable layer 5 to a small area such as zone 8 for example. A larger zone 7 might however be required if it is desired to modify the shape of the flat article over a larger area or at the edges. The area of the zone is thus a matter of choice according to the circumstances prevailing and the exact size required can easily be determined.

Figure 5:
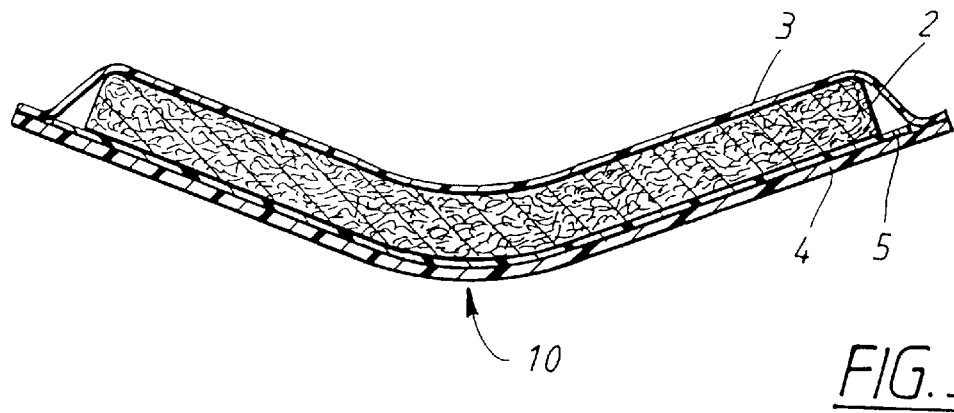
FIG. 5 shows a sectional side view of a sanitary pad made in accordance with the invention starting from the initial stage as shown in FIG. 1.

The view shown in FIG. 5 is the same as that in FIG. 1 except that the thermoformable layer 5 has been thermoformed by the application of heat and a restraining force so as to assume the bowed shape desired. Since the thermoformed layer is integrated into the structure of the absorbent article, its bowed shape is also transferred to the whole of the article.

The method of production of the article may vary. However, considering the example of FIG. 1 and FIG. 5, the thermoformable layer 5 may be added to the back sheet 4 and then the combined back sheet layer 4 and layer 5 moved to a further station in which the absorbent core 2 is placed thereon. A top sheet 3 is then added which is then sealed around its edge 11 to the layer 4. All this may occur in the flat state of the article and may be an in-line procedure with a plurality of articles still joined together.

The article, or joined articles, is/are then transferred to a thermoforming station in which the article is made to assume a predetermined three-dimensional shape by being placed onto or into a male or female mould for example. Heat is then applied for a specified time (for example as indicated previously above) by appropriate means and the article then allowed to cool naturally or by forced cooling.

Once cooled, the thermoformable layer will have been thermoformed and thus substantially maintain the shape which it assumed whilst in the mould. Due to its integration between the layers 2 and 4, the whole article is thus maintained substantially in the new shape.

Clearly for such absorbent articles it is important that flexibility is maintained in order to adapt to different body shapes and to accommodate movement. Thus the thermoformable material must still be adequately flexible after thermoforming.

Thus, although a three-dimensional article has been formed it has not been necessary to stretch any of the layers and hold them in place whilst a further layer is attached. Instead the layers merely need to be constrained in a particular shape whilst heat is applied. Where it proves beneficial to integrate the layer 5 into the core 2, such as in FIG. 2, the further advantage is provided that the mat-building step of the absorbent core can still be carried out in the flat condition.

In certain cases it may be desirable to only adapt the shape of one of the layers (embodiment not depicted). Such a case might be where it is desirable to form only the back sheet layer into a dished form in a way which allows it to partially enclose the absorbent core 2. This can be achieved by separate thermoforming of the thermoformable layer in conjunction with the backing sheet by itself, with only subsequent addition of the absorbent core and top sheet. Alternatively the edge regions of the backing sheet might be thermoformed whilst the back sheet layer is held in a mould of some type to keep the remainder flat.

Figure 6:
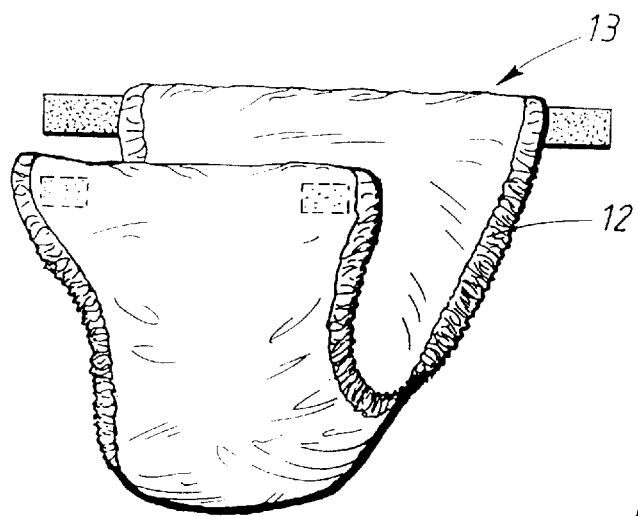
FIG. 6 shows a perspective view of a nappy made in accordance with the present invention.

FIG. 6 shows a further product to which this technology may be applied. Nappies or diapers 13 for infants or adults of the basic type as in FIG. 6, but having a flat form, are traditionally made by machinery which applies seams in two different directions, one of these being opposed to the direction of travel in the machinery. Various webs and seals are often also applied to obtain a type of three-dimensional structure when the nappy is folded out. However by use of the thermoformable layer in a manner according to the invention a more precise or complicated shape can be given to the nappy and a shape which is substantially maintained in the relaxed state which would allow it to perform its various functions more efficiently and possibly also with reduced materials. For example, the shape shown in FIG. 6 may easily be achieved by thermoforming a layer 5 in said nappy to give the required curvature. The leg elastics 12 are still present and these merely assist adaptation to the user's legs during all movements. Similarly waist elastic may also be present.

Shaped incontinence protection pads or chassis of large or small type may also be formed in a similar way to that described above.

The invention is not restricted to the embodiments described above but may be varied widely within the scope of the appended claims.

I claim:

1. Flexible absorbent article for use in absorbing bodily fluids, said article comprising:

a plurality of layers including an absorbent core, wherein one or more of said layers has a three-dimensional shape defining an open volume therewithin, and a thermoformed layer formed integrally with said plurality of layers, said thermoformed layer substantially maintaining said one or more layers in said three-dimensional shape, wherein said thermoformed layer is in the form of a net which is integrally thermoformed with said one or more layers.

2. The flexible absorbent article according to claim 1, wherein said article is a sanitary pad.

3. The flexible absorbent article according to claim 1, wherein said article is an absorbent garment.

4. The flexible absorbent article according to claim 1, wherein the absorbent core is located between a backing sheet layer and a top sheet layer and said three-dimensional shape is given to the backing sheet layer so as to form a dished carrier for the remaining layers.

5. The flexible absorbent article according to claim 1, wherein said three-dimensional shape is provided in all layers of the article.

6. The flexible absorbent article according to claim 1, wherein the absorbent core is located between a backing sheet layer and a top sheet layer and in that said thermoformed layer is located at a position between the backing sheet layer and the top sheet layer.

7. The flexible absorbent article according to claim 1, wherein said thermoformed layer is positioned within said absorbent core.

8. The flexible absorbent article according to claim 4, wherein said thermoformed layer is integral with said backing sheet layer.

9. The flexible absorbent article according to claim 3, wherein said article is a diaper for infants or adults.

10. The flexible absorbent article according to claim 1, wherein said net includes longitudinal and transverse crossing threads or fibers.

11. Method of manufacture of an absorbent article comprising a plurality of layers including an absorbent core, said method comprising:

adding a thermoformable layer to one of said plurality of layers either before, during or after the manufacture of said one of said plurality of layers, wherein said one of said plurality of layers is made to assume a predetermined three-dimensional shape defining an open volume therewithin, and wherein said thermoformable layer is in the form of a net; and applying heat to said one of said plurality of layers and said thermoformable net layer whilst said one of said plurality of layers and said thermoformable net layer are in said predetermined shape so as to thermoform them substantially in accordance with said predetermined shape.

12. The method of manufacture of an absorbent article according to claim 11, wherein said one of said plurality of layers is made to assume said three-dimensional shape initially by being placed onto, or into, a mold.

13. The method of manufacture of an absorbent article according to claim 11, wherein said absorbent core comprises a mat-built core of cellulosic fibres, and said thermoformable net layer is added during mat-building so as to be fully integrated into said absorbent core.

14. The method of manufacture of an absorbent article according to claim 11, wherein said net is formed by longitudinal and transverse crossing threads or fibers.

\* \* \* \* \*

UNITED STATES PATENT AND TRADEMARK OFFICE
CERTIFICATE OF CORRECTION

PATENT NO.   : 5,961,509
DATED        : October 5, 1999
INVENTOR(S)  : Robert KLING It is certified that error appears in the above-indentified patent and that said Letters Patent is hereby corrected as shown below:

At Col. 2, line 14, "Lo" should be --to--.

At Col. 3, lines 53-54, "taco zones 7 and 8 one depicted. These zones defile" should be --two zones 7 and 8 are depicted. These zones define--.

Signed and Sealed this

Thirteenth Day of June, 2000

Attest:

Q. TODD DICKINSON

*Attesting Officer*          *Director of Patents and Trademarks*